(12) United States Patent
Hsieh

(10) Patent No.: US 6,278,767 B1
(45) Date of Patent: Aug. 21, 2001

(54) METHODS FOR MEASURING CURVED DISTANCES ON 3D AND MIP IMAGES

(75) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/301,032

(22) Filed: Apr. 28, 1999

(51) Int. Cl.[7] ........................................ A61B 6/04
(52) U.S. Cl. ............................. 378/163; 382/131
(58) Field of Search .................... 378/163, 15, 14, 378/162, 164, 8, 21, 24, 25, 26, 27; 382/131, 288, 286

(56) References Cited

U.S. PATENT DOCUMENTS 4,099,880 * 7/1978 Kano ..................................... 356/164
5,825,908 * 10/1998 Pieper et al. ........................ 382/131

* cited by examiner

*Primary Examiner*—Robert H. Kim
*Assistant Examiner*—Irakli Kiknadze
(74) *Attorney, Agent, or Firm*—Armstrong Teasdale LLP; Christian G. Cabou

(57) ABSTRACT

The present invention, in one form, is an imaging system for accurately determining a length of an object of interest (OOI). Particularly and in one embodiment, the OOI has a curvature in a direction non-parallel to a projection plane. Initially, after utilizing MIP images to identify the OOI, boundaries and a center of the OOI are determined for each image. Utilizing the determined boundaries and center, an OOI length is determined. Specifically, the OOI length is determined by determining a distance between each adjacent image and then summing the resulting values. The distance is then displayed on the MIP images by either distance indicators or numerical display.

32 Claims, 2 Drawing Sheets

METHODS FOR MEASURING CURVED DISTANCES ON 3D AND MIP IMAGES

BACKGROUND OF THE INVENTION

This invention relates generally to computed tomography (CT) imaging and more particularly, to measuring curved distances of an object of interest utilizing maximum intensity projection (MIP) images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

At least one known CT imaging system is configured to perform CT angiograghy (CTA). Compared to a conventional x-ray angiogram, the CTA system is advantageous as result of being non-invasive and more cost effective. In performing a CTA procedure, a set of CT images are first acquired and a Maximum Intensity Projection (MIP) image is generated to mimic the appearance of an x-ray angiogram. To measure the length of a section, or segment, of a vessel, several points are identified in the MIP image. A set of straight line distances between two points are then measured. For straight vessels that are perpendicular to the direction of projection, such a procedure yields satisfactory results. However, known CTA systems are unable to accurately measure a distance of a vessel segment being curved in a direction non-parallel to a MIP projection plane. As a result, known CTA systems typically underestimate the length of the vessel.

At least one known x-ray angiography system overcomes the difficultly of measuring curved vessels by placing a specially designed catheter inside the vessel. The catheter includes a series of uniformly spaced beads to provide distance markers on the angiography images. The distance between two points is determined by counting the number of beads in the x-ray image. However, as described above, such x-ray systems are invasive and very costly.

It would be desirable to provide an system which facilitates accurate measurement of vessel segment. It would also be desirable to provide such a system which facilitates retrospective selection of any vessel segment.

BRIEF SUMMARY OF THE INVENTION

These and other objects may be attained in a system which, in one embodiment, includes a measurement algorithm that accurately determines a length of at least a segment of a object of interest. Particularly and in one embodiment, the object of interest is a blood vessel having a curvature in a direction orthogonal to a projection plane.

Specifically, and in accordance with one embodiment of the present invention, a plurality of Maximum Intensity Projection (MIP) images are generated from reconstructed computed tomography (CT) images generated from projection data acquired in a scan. After identifying the object of interest, boundaries are determined for the object of interest utilizing a first CT image. Boundaries of the object of interest in neighboring CT images are then determined using the first image boundaries. Specifically and in one embodiment, the boundaries are determined as a location where the intensity of the image is within a pre-determined percentage of the difference between an object of interest intensity and a background intensity and the region determined by the boundaries is connected with the region from a previous slice. Utilizing the boundaries, a center of the object of interest is determined for each CT image.

Utilizing the determined center and boundaries for each image, a length of the object of interest is determined. Specifically, the length of the object of interest is determined by determining a distance between each adjacent image and then summing the resulting values. Particularly and in one embodiment, utilizing the determined center and boundaries in the adjacent images, the length of a segment of the object of interest is determined in accordance with:

$$\Delta = \sqrt{\Delta_x^2 + \Delta_y^2 + \Delta_z^2},$$

where:

$\Delta x$=a difference between centers of the object of interest in adjacent images in the x-direction;

$\Delta y$=a difference between centers of the object of interest in adjacent images in the y-direction; and $\Delta z$=an interval, or spacing, between adjacent images in the z-direction.

In one embodiment, the system displays a plurality of distance indicators along with the image of the object of interest so that an operator is able to determine the length of the object of interest. Particularly, each distance indicator represents a pre-determined distance so that by counting the number of distance indicators the total length of the object of interest is quickly determined by the operator. In one embodiment, the intensity level of the distance indicators may be altered so the intensity of the indicators is greater than or less than the intensity of the object of interest.

The above described system facilitates accurate measurement of an object of interest. More specifically and in one embodiment, the above described system includes a measurement algorithm for determining the length of at least a segment of a blood vessel. In addition, such algorithm facilitates the retrospective selection of any object of interest by the operator.

DETAILED DESCRIPTION OF THE INVENTION

Figure 1:
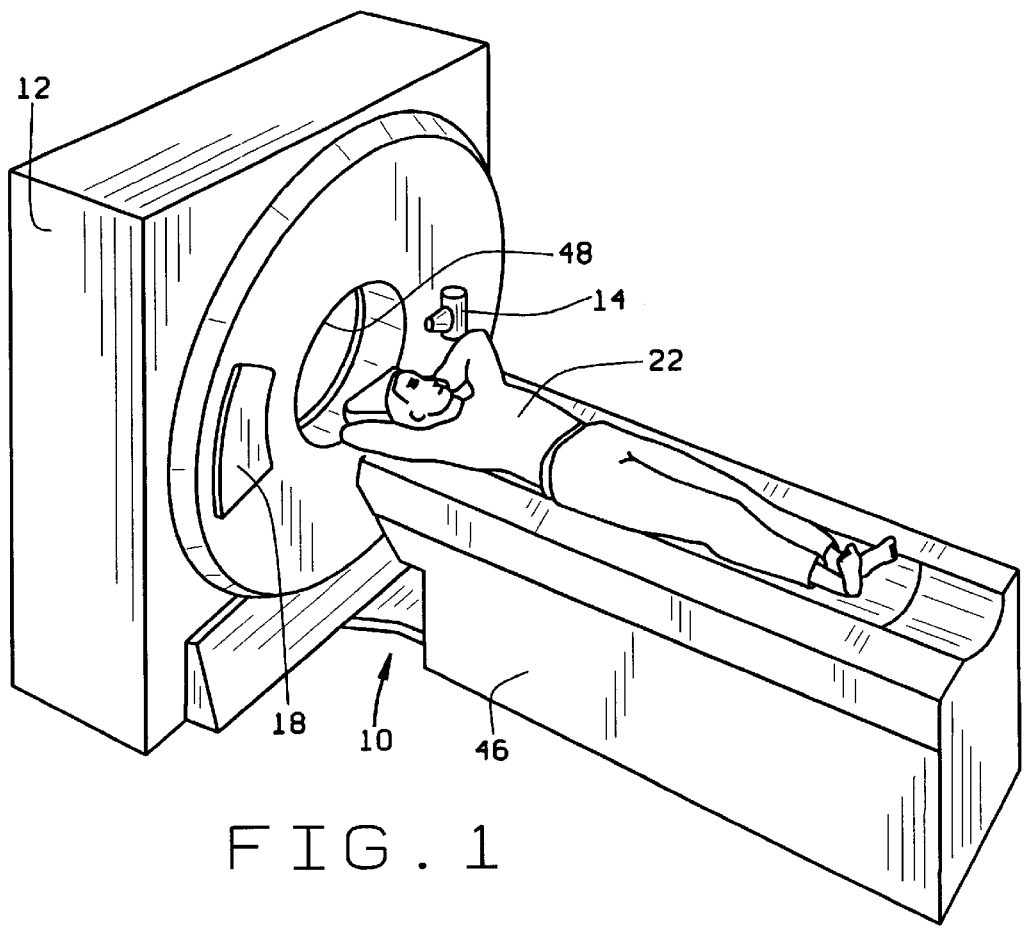
FIG. 1 is a pictorial view of a CT imaging system.
Figure 2:
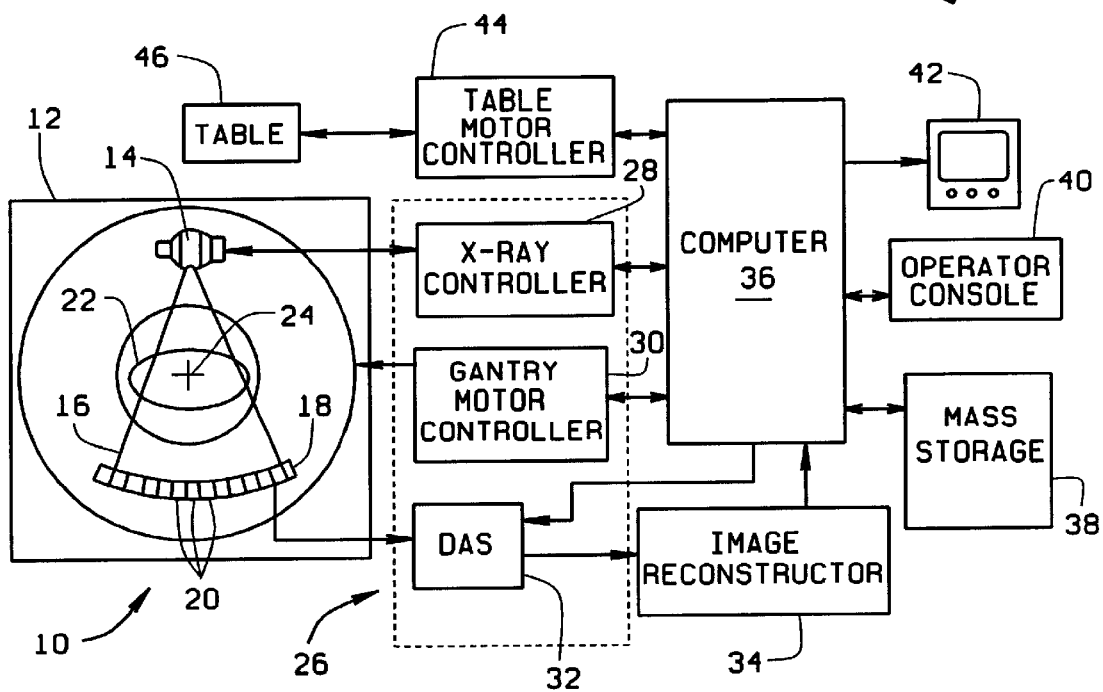
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has at least one input device such as a keyboard (not shown) or a pointing device, for example, a mouse (not shown). An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In accordance with one embodiment of the present invention, a measurement algorithm determines a length of an object of interest having a curvature. The present algorithm is not directed to, nor limited to practice with, any particular helical or axial method scanning.

Also, although the present measurement algorithm is sometimes described herein in connection with a third generation CT system, the present algorithm can be practiced in connection with many other types of CT systems, including fourth generation CT systems. In addition, the algorithm may be used with other types of tomographic systems, such as MR. Further, in one embodiment, the measurement algorithm is implemented in computer 36 and processes, for example, data stored in mass storage 38. Many other alternative implementations are, of course, possible.

Initially, to determine a length of an object of interest (OOI) 50, system utilizes a complete set of reconstructed image data, including three-dimensional data of object of interest 50, to generate Maximum Intensity Projection (MIP) images, as known in the art. Specifically, and in one embodiment, to generate a MIP image, a direction of forward projection is determined and a maximum pixel value along each forward projection ray is identified. The projection value is then assigned to this maximum pixel value. Utilizing this procedure a plurality of MIP images are generated.

Figure 3:
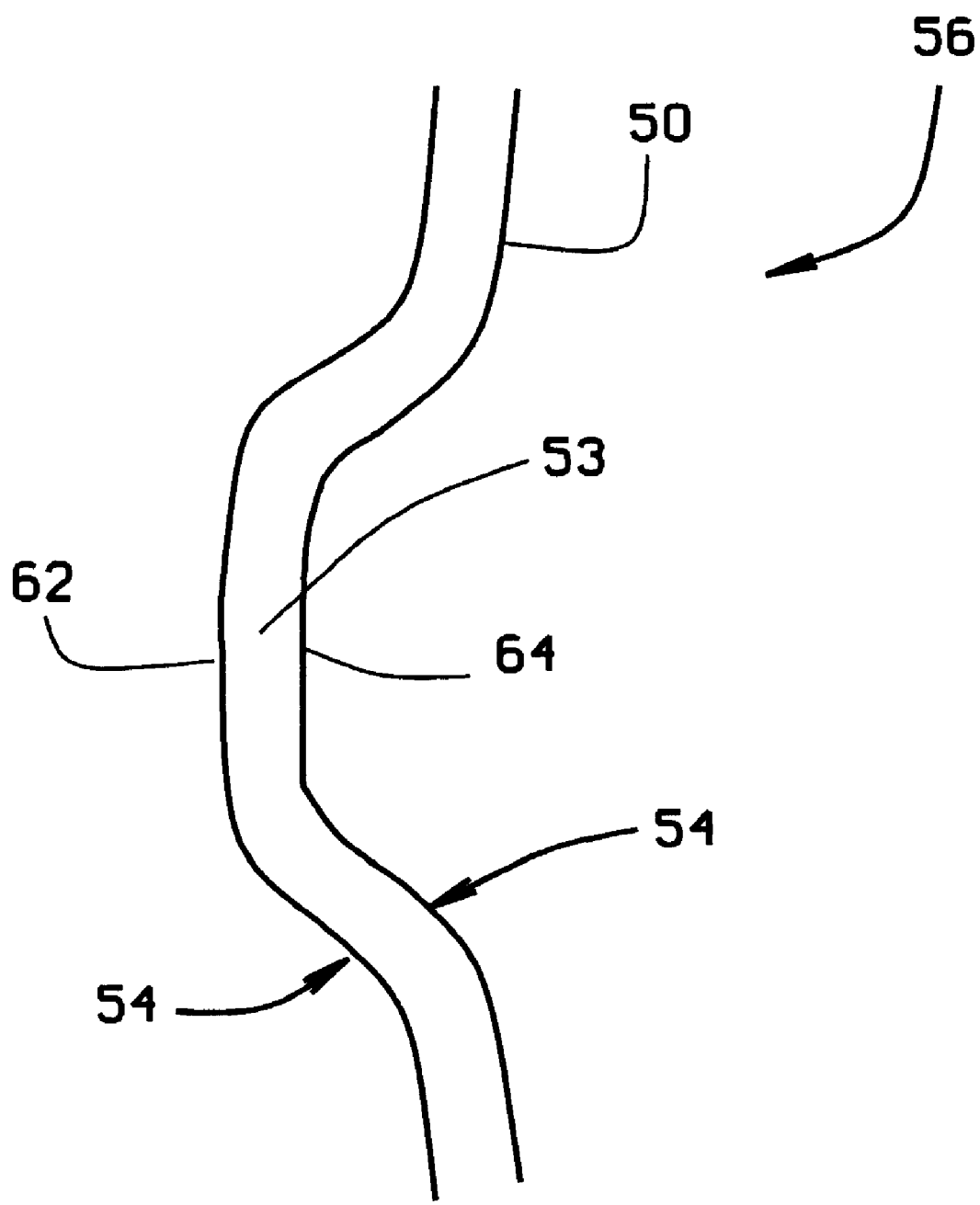
FIG. 3 is a pictorial view of an object of interest.

In accordance with one embodiment of the present invention and as shown in FIG. 3, a specific OOI 50 to be measured is initially identified and boundaries 54 of OOI 50 are determined. Utilizing the determined boundaries, a total length of OOI 50 is determined. In one embodiment, OOI 50 is at least a portion of a blood vessel, an intestine or other tissue of the body (not shown). More specifically and in one embodiment, initially, a cursor (not shown) is placed within, or an interior of, OOI 50, for example near a center 58, in a first CT image 56. In one embodiment, the operator places the cursor near center 58 using the mouse based upon the image on display 42.

In another embodiment, system 10, specifically computer 36 or image reconstructor 34, is configured to more accurately position the cursor by performing a search of the CT image data. More specifically, using at least one known algorithm, computer 36 examines a first CT image 56 to determine where the intensity of the image is within a pre-determined fraction, or percentage of the intensity between OOI 50 and a background (not shown).

A boundary 62 of OOI 50 is defined by system 10 as where the intensity is equal to the pre-determined fraction. Utilizing a similar process, system 10 determines, or identifies the location of second boundary 64. By performing boundary determinations for a plurality of orientations, or locations, cross-sectional data of OOI 50 is generated. More specifically, utilizing the plurality of determined boundary locations from each orientation, a three dimensional center 58 of OOI 50 is determined for CT image 56. For example, after placing the cursor near center 58, the location of boundaries 62 and 64 are defined, or determined, by where the intensity is within the pre-determined fraction. Utilizing boundaries 62 and 64, the three-dimensional location of center 58 is determined.

In an alternative embodiment, system 10, specifically computer 36 or image reconstructor 34, utilizes a centroid value of a region (not shown) within boundaries 62 and 64 to determine a location of OOI center 58. Of course, other known methods may be utilized to determine a location of center 58 and boundaries 62 and 64. For example and in one embodiment, a template matching to an oval shape method may be used. In another embodiment using the described process, a length of a vessel wall 70 of OOI 50 is determined by placing the cursor at boundary 62 or 64 of the vessel 50 in CT image 56.

In one embodiment, after determining boundaries 62 and 64 and center 58 in first CT image 56, first and second boundaries (not shown) are determined for each of the remaining plurality of CT images (not shown). More specifically, for each CT image, the boundaries of OOI 50 are determined utilizing a center from an adjacent, or neighboring, CT image. Particularly, utilizing the determined center from a neighboring image as a seed, or initial, location, computer 36 or image processor 34 utilizes the above described process to determine the boundaries of OOI in each reconstructed CT image. For example, utilizing center 58 from first image 56 as an initial location, boundaries are determined for a second image. Utilizing the results of this process, boundaries are determined for each subsequent image. In one embodiment, after determining the boundaries of each CT image, a center is determined for each image based upon the determined boundaries of the respective image. Particularly, and as described above, three dimensional boundaries are utilized to determine a center location of OOI 50.

After determining the boundaries and center for each respective reconstructed CT image, a length of OOI 50 is determined. More specifically, in order to determine a length of OOI 50, a distance is determined between each adjacent image and then summing the resulting values. Particularly and in one embodiment, the distance of a segment (not shown) of OOI 50 between the centers in adjacent images is determined in accordance with:

$$\Delta = \sqrt{\Delta_x^2 + \Delta_y^2 + \Delta_z^2},$$

where:
66 x=a difference between the centers of OOI 50 in adjacent images in the x-direction;
Δy=a difference between the centers of OOI 50 in adjacent images in the y-direction; and
Δz=an interval, or spacing, between adjacent images in the z-direction.

In one embodiment, Δ, approximates a length of an OOI segment 50 by a straight line segment. However, as a result of the very small distance between adjacent images in system 10, typically, for example, a few millimeters, the amount of approximation error of the length is quite small.

In an alternative embodiment, system 10 also includes a curve fitting algorithm to determine the length of the OOI segment. More specifically and in one embodiment, the curve fitting algorithm is executed in computer 36 or image reconstructor 36 and utilizes the center of each CT image to determine a curved distance of each segment of OOI 50.

In order to determine a total length of OOI 50, the length or distance of each segment is summed or added together. More specifically and in one embodiment, the total length, T, is determined in accordance with:

$$\sum_{i=1}^{i=N-1} \Delta_i,$$

where:
N equals a total number of CT images and
Δi equals a length of an OOI segment in CT image i.

In one embodiment, the total length, T, of OOI 50 is then displayed to the operator as a numerical value using console 40. In another embodiment, the operator may wish to determine the length of a specific portion of OOI 50. More specifically, utilizing the input device of console 40, the operator selects, or chooses, the specific portion of OOI 50. As a result of the one to one correspondence between a vertical location on the MIP images and a CT reconstructed images, the above described distance determinations may be made utilizing the reconstructed CT images.

In one embodiment, system 10 displays along with the OOI image, at least one distance indicator to assist the operator in determining the length of object of interest 50. More specifically, the length of OOI 50 may be quickly determined by the operator by counting the number of distance indicators which are visually overlaid or combined with the image of OOI 50. Particularly, after determining the total length of OOI 50, the appropriate number of distance indicators are overlaid on the image of OOI 50. Each distance indicator represents a pre-determined distance value and is placed along OOI 50 so that the length of OOI 50 is quickly determined by the operator by counting the number of indicators and multiplying by a pre-determined distance for each indicator. For example, where display 42 displays a reconstructed image of at least a portion of OOI 50 having five distance indicators and each distance indicator represents 3 cm, the total length, T, of the displayed portion of OOI 50 is 15 cm (3 cm×5).

In one embodiment, an intensity of each distance indicator is alterable relative to an intensity of the image of OOI 50 so that the distance indicators have an intensity level higher or lower than OOI 50. In another embodiment, the distance indicators are displayed in a different color different than that of OOI 50. Use of the distance indicators in system 10 provides information to the operator for a similar look and feel as an x-ray angiography thereby reducing training time and the probability of error.

After determining the distance of a first OOI 50, system 10 allows the user or operator to determining a length or distance of any number of additional objects of interest in a retrospective fashion. More specifically, after determining the length of OOI 50, the operator selects any number of additional objects of interest and determines a length of each OOI in the manner described above.

The above described system facilitates accurate measurement of an object of interest. More specifically and in one embodiment, the above described system includes a measurement algorithm for determining the length of at least a segment of a blood vessel. In addition, such algorithm facilitates the retrospective selection of any object of interest by the operator.

In other embodiments of the present invention, the distance measurement and the placement of the distance indicators can be applied to other types of 3D images, e.g., volume rendering, 3D shaded surface display or virtual endoscopy images).

In another embodiment, the distance indicator can be toggled "on" and "off" in the display. In this manner, the operator can see the area blocked by the distance indicator.

In yet another embodiment, the present invention is utilized with other tomographic modalities, such as MR, ultrasound, or optical tomography.

While the invention has been described in terms of various specific embodiments, those skilled in the art will recognize that the invention can be practiced with modifications within the spirit and scope of the claims. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Moreover, the system described herein performs an axial scan, however, the invention may be used with a helical scan although more than 360° of data are required.

What is claimed is:

1. A method for determining a length of an object using tomographic images generated in an imaging system, said method comprising:

identifying an object of interest, the object of interest having a curvature;

determining boundaries of the object of interest;

determining a three-dimensional length of the object of interest;

overlaying a plurality of distance indicators representing predetermined distances along the length of the object of interest on an image of the object of interest; and displaying the image of the object of interest including the overlaid distance indicators, wherein a distance along a selected portion of the length of the object of interest is indicated by a count of the plurality of distance indicators along the selected portion.

2. A method in accordance with claim 1 wherein identifying an object of interest comprises identifying at least a portion of a tissue in a body.

3. A method in accordance with claim 1 wherein identifying an object of interest comprises identifying a location of the object of interest on a first tomographic image.

4. A method in accordance with claim 3 wherein identifying a location of the object of interest on a first tomographic image comprises an operator placing a location cursor at an interior of the object of interest.

5. A method in accordance with claim 3 wherein an identifying a location of the object of interest on a first tomographic image comprises an operator placing a location cursor on a wall of the object of interest.

6. A method in accordance with claim 1 further comprising altering an intensity of a distance indicator.

7. A method in accordance with claim 1, wherein displaying the image of the object of interest including the overlaid distance indicators comprises displaying the distance indicators in a color different from that of the object of interest.

8. A method for determining a length of an object using tomographic images generated in an imaging system, said method comprising:

identifying an object of interest, the object of interest having a curvature;

determining boundaries of the object of interest;

determining a three-dimensional length of the object of interest;

overlaying a plurality of distance indicators representing predetermined distances along the length of the object of interest on an image of the object of interest; and displaying the image of the object of interest including the overlaid distance indicators, wherein a distance along a selected portion of the length of the object of interest is indicated by a count of the plurality of distance indicators along the selected portion;

wherein determining boundaries of the object of interest comprises generating cross-section data for the object of interest utilizing a first tomographic image.

9. A method in accordance with claim 8 further comprising identifying a center of the object of interest utilizing a first tomographic image.

10. A method in accordance with claim 9 further comprising determining the boundaries of the object of interest in each tomographic image.

11. A method in accordance with claim 10 wherein determining boundaries of the object of interest in each tomographic image comprises determining the boundaries of the object of interest in each tomographic image utilizing the identified center and the cross-sectional data from an adjacent tomographic image.

12. A method in accordance with claim 10 further comprising determining a center of the object of interest in each tomographic image.

13. A method in accordance with claim 12 wherein determining a three-dimensional length of the object of interest comprises determining a length of the object of interest utilizing the determined centers of the object of interest.

14. A method in accordance with claim 13 wherein determining a length of the object of interest utilizing the determined centers of the object of interest comprises determining a length of a segment, $\Delta$, of the object of interest, in accordance with:

$$\Delta = \sqrt{\Delta_{x^2} + \Delta_{y^2} + \Delta_{z^2}},$$

where:

$\Delta x$ = a difference between centers of object of interest in adjacent images in the x direction;

$\Delta y$ = a difference between centers of object of interest in adjacent images in the y direction; and $\Delta z$ = an interval between adjacent images in the z direction.

15. A method in accordance with claim 14 further comprising determining a total length, T, of the object of interest, wherein the total length is determined in accordance with:

$$\sum_{i=1}^{i=N-1} \Delta i,$$

where:

N equals a total number of tomographic images.

16. A method in accordance with claim 12 wherein determining a three-dimensional length of the object of interest comprises performing a curve fit of the centers of the object of interest.

17. A computed tomography (CT) system for determining a length of an object using images generated in a tomography system, said tomography system comprising an x-ray source for producing an x-ray beam along a projection plane and a detector array, said tomography system configured to:

identify an object of interest, the object of interest having a curvature;

determine boundaries of the object of interest;

determine a three-dimensional length of the object of interest;

overlay a plurality of distance indicators representing predetermined distances along the length of the object of interest on an image of the object of interest; and display the image of the object of interest including the overlaid distance indicators, wherein a distance along a selected portion of the object of interest is indicated by a count of the plurality of distance indicators along the selected portion.

18. A system in accordance with claim 17 wherein to identify an object of interest, said system configured to identify at least a portion of a tissue in a body.

19. A system in accordance with claim 17 wherein to identify an object of interest, said system configured to identify a location of the object of interest on a first tomographic image.

20. A system in accordance with claim 19 wherein to identify a location of the object of interest on a first tomographic image, said system configured to allow an operator to place a location cursor at an interior of the object of interest.

21. A system in accordance with claim 19 wherein to identify a location of the object of interest on a first tomographic image, said system configured to allow an operator to place a location cursor on a wall of the object of interest.

22. A system in accordance with claim 17 wherein an intensity of each said distance indicator is alterable.

23. A system in accordance with claim 17 further configured to display said distance indicators in a color different from that of the object of interest.

24. A computed tomography (CT) system for determining a length of an object using images generated in a tomography system, said tomography system comprising an x-ray source for producing an x-ray beam along a projection plane and a detector array, said tomography system configured to:

identify an object of interest, the object of interest having a curvature;

determine boundaries of the object of interest;

determine a three-dimensional length of the object of interest;

overlay a plurality of distance indicators representing predetermined distances along the length of the object of interest on an image of the object of interest; and display the imaging of the object of interest including the overlaid distance indicators, wherein a distance along a selected portion of the object of interest is indicated by a count of the plurality of distance indicators along the selected portion;

wherein to determine boundaries of the object of interest, said system configured to generate cross-section data for the object of interest utilizing a first tomographic image.

25. A system in accordance with claim 24 further configured to identify a center of the object of interest utilizing a first tomographic image.

26. A system in accordance with claim 25 further configured to determine boundaries of the object of interest in each tomographic image.

27. A system in accordance with claim 26 wherein to determine boundaries of the object of interest in each tomographic image, said system configured to determine said boundaries of the object of interest in each tomographic image utilizing said identified center and said cross-sectional data from an adjacent tomographic image.

28. A system in accordance with claim 26 further configured to determine a center of the object of interest in each tomographic image.

29. A system in accordance with claim 28 wherein to determine a three-dimensional length of the object of interest, said system configured to determine a length of the object of interest utilizing said determined centers of the object of interest.

30. A system in accordance with claim 29 wherein to determine a length of the object of interest utilizing said determined centers of the object of interest, said system configured to determine a length of a segment, $\Delta$, of the object of interest, in accordance with:

$$\Delta = \sqrt{\Delta_x^2 + \Delta_y^2 + \Delta_z^2},$$

where:

$\Delta x$ = a difference between said centers of object of interest in adjacent images in the x direction;

$\Delta y$ = a difference between said centers of object of interest in adjacent images in the y direction; and $\Delta z$ = an interval between adjacent images in the z direction.

31. A system in accordance with claim 30 further configured to determine a total length, T, of the object of interest, wherein said total length is determined in accordance with:

$$\sum_{i=1}^{i=N-1} \Delta_i,$$

where:

N equals a total number of tomographic images.

32. A system in accordance with claim 28 wherein to determine a three-dimensional length of the object of interest, said system configured to perform a curve fit of said centers of the object of interest.

* * * * *

UNITED STATES PATENT AND TRADEMARK OFFICE
CERTIFICATE OF CORRECTION

PATENT NO. : 6,278,767 B1
DATED : August 21, 2001
INVENTOR(S) : Jiang Hsieh

It is certified that error appears in the above-identified patent and that said Letters Patent is hereby corrected as shown below:

Column 2,
Line 36, delete "$\Delta = \sqrt{\Delta_{x^2 + \Delta_y^2 + \Delta_z^2}}$" and insert therefor -- $\Delta = \sqrt{\Delta x^2 + \Delta y^2 + \Delta z^2}$ --.

Column 3,
Line 64, between "system" and "utilizes" insert -- 10 --.

Column 5,
Line 15, delete "$\Delta = \sqrt{\Delta_{x^2 + \Delta_y^2 + \Delta_z^2}}$" and insert therefor -- $\Delta = \sqrt{\Delta x^2 + \Delta y^2 + \Delta z^2}$ --.

Line 18, delete "66" and insert therefor -- $\Delta$ --.

Column 8,
Line 5, delete "$\Delta = \sqrt{\Delta_{x^2 + \Delta_y^2 + \Delta_z^2}}$" and insert therefor -- $\Delta = \sqrt{\Delta x^2 + \Delta y^2 + \Delta z^2}$ --.

Column 10,
Line 13, delete "$\Delta = \sqrt{\Delta_{x^2 + \Delta_y^2 + \Delta_z^2}}$" and insert therefor -- $\Delta = \sqrt{\Delta x^2 + \Delta y^2 + \Delta z^2}$ --.

Signed and Sealed this

Thirteenth Day of May, 2003

JAMES E. ROGAN
*Director of the United States Patent and Trademark Office*